United States Patent [19]

Haerten et al.

[11] 4,077,405

[45] Mar. 7, 1978

[54] APPARATUS FOR INFUSING LIQUIDS INTO HUMAN OR ANIMAL BODIES

[75] Inventors: Rainer Haerten; Heinz Kresse, both of Erlangen, Germany

[73] Assignee: Siemens Aktiengesellschaft, Berlin & Munich, Germany

[21] Appl. No.: 669,459

[22] Filed: Mar. 22, 1976

[30] Foreign Application Priority Data

Mar. 26, 1975 Germany ............................ 2513467

[51] Int. Cl.$^2$ ............................................. A61M 5/14
[52] U.S. Cl. .................. 128/214 F; 128/213; 128/214 E; 128/260; 128/DIG. 12; 128/DIG. 13
[58] Field of Search ....... 128/214 F, 214 E, DIG. 12, 128/DIG. 13, 273, 274, 214 R, 213, 260; 138/45, 46; 3/1

[56] References Cited

U.S. PATENT DOCUMENTS

| 3,023,750 | 3/1962 | Baron | 128/214 F |
|---|---|---|---|
| 3,052,238 | 9/1962 | Broman et al. | 128/214 F |
| 3,559,644 | 2/1971 | Stoft | 128/214 F |
| 3,648,694 | 3/1972 | Mogos et al. | 128/214 F |
| 3,731,681 | 5/1973 | Blackshear et al. | 128/214 F |
| 3,800,794 | 4/1974 | Georgi | 128/214 E |
| 3,837,339 | 9/1974 | Aisenberg et al. | 128/213 |
| 3,841,354 | 10/1974 | McDonnell | 128/214 R X |
| 3,894,538 | 7/1975 | Richter | 128/260 |

FOREIGN PATENT DOCUMENTS

| 2,106,275 | 8/1972 | Germany | 128/214 E |
|---|---|---|---|
| 1,383,594 | 2/1975 | United Kingdom. | |

*Primary Examiner*—Robert W. Michell
*Assistant Examiner*—Michael H. Thaler
*Attorney, Agent, or Firm*—Hill, Gross, Simpson, Van Santen, Steadman, Chiara & Simpson

[57] ABSTRACT

Apparatus for feeding liquids, particularly medications such as insulin, or the like, to humans or animals comprising a supply reservoir for the liquid, a conveying arrangement connected to the supply reservoir and including a pressure generating device for feeding the liquid by pressure application from the supply reservoir to the body, and a controllable dosing arrangement for producing a desired rate of infusion. The pressure generating device includes an overpressure generator which constantly maintains the liquid present in the supply reservoir under overpressure as distinct from the pressure prevailing at the point of liquid discharge. The dosing arrangement comprises a pilot or switching valve for periodically releasing liquid from the supply reservoir to the body, the switching valve being switchable for the purpose of fine dosing by the discharge of preselectable constant volumes of liquid at periodic intervals predeterminable in accordance with the treatment program.

10 Claims, 7 Drawing Figures

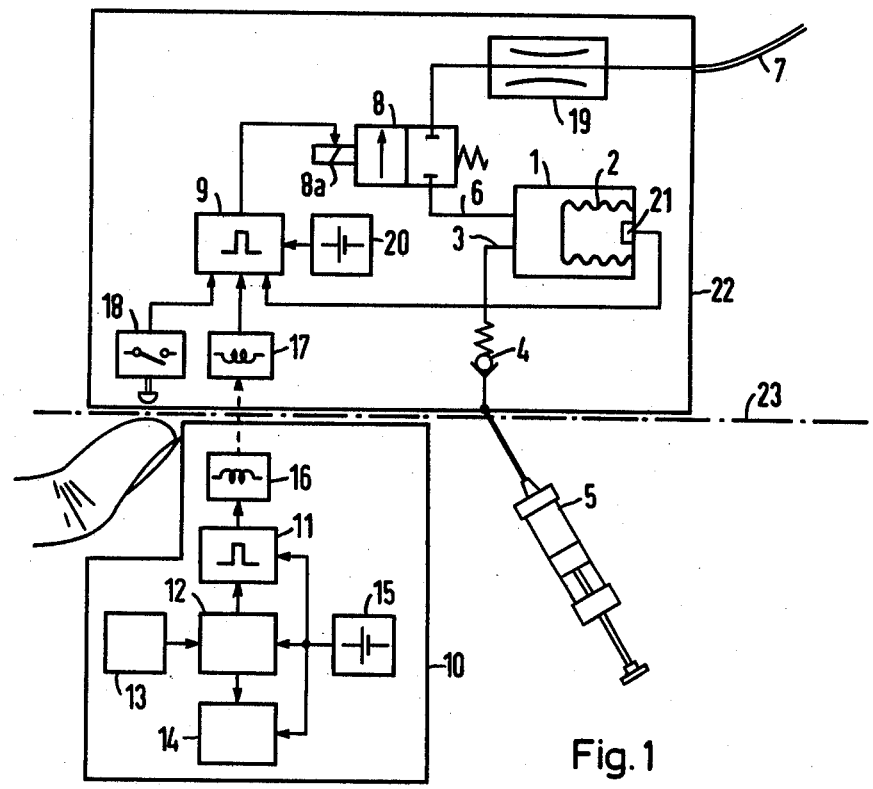
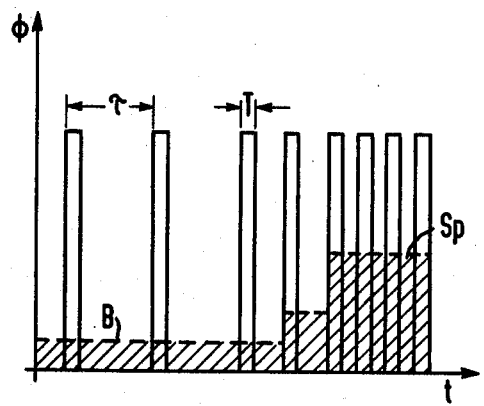
Fig. 2
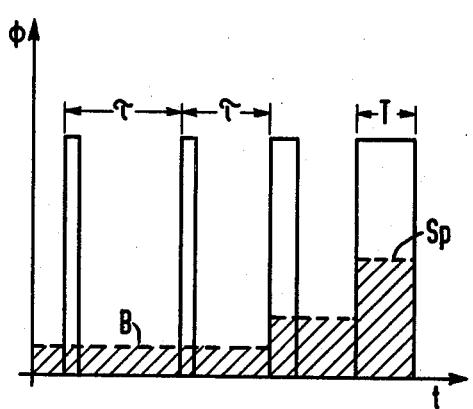
Fig. 3

APPARATUS FOR INFUSING LIQUIDS INTO HUMAN OR ANIMAL BODIES

FIELD OF THE INVENTION

The present invention relates to apparatus for infusing liquids, and more particularly medications such as insulin, or the like, into human or animal bodies, said apparatus comprising a supply reservoir for the liquid and a conveying device which, for the purpose of feeding the liquid from the supply reservoir to the body, comprises a pressure generator for infusing the liquid by means of pressure application, and a controllable dosing device for producing the desired rates of infusion.

BACKGROUND AND PRIOR ART

In the treatment of patients, more particularly with liquid medications, a fixed, adjusted rate of infusion is often insufficient, and it is necessary that the amount of liquid infused per time unit has to be adjusted repeatedly at certain time intervals. Such a readjustment is particularly required if insulin is to be infused continuously in the treatment of diabetes, because the insulin requirement of the diabetic patient is subject to substantial fluctuations during the daytime, said fluctuations being caused, for example, by the cycle of meals, while it is nearly constant in time during night hours. An implantable apparatus of the above type, which primarily serves for the controlled feeding of insulin, is known, for example, from U.S. Pat. No. 3 894 538. This known device operates according to the electro-osmotic principle, i.e., the discharge or administering of insulin is controlled or regulated by the fact that particles of gas or liquid migrate in electro-osmotic manner into a first receptacle having a variable volume, which migration of said particles takes place in dependence on electrical signals applied to electrodes. As a result of the volume expansion of said receptacle, a separating diaphragm is deflected into a second receptacle serving as the receptacle which contains the medication, whereby the medication is expelled from said second receptacle in the desired amount, or dose.

Furthermore, a device is known from U.S. Pat. No. 3 837 339 in which the glucose level in the human body is continuously measured by means of an implantable glucose sensor, and a switching signal is emitted by a voltage comparator to a switching valve if said level rises beyond a predeterminable value. The switching valve so activated connects the blood circulatory system of the controlled patient with an insulin-containing receptacle which, for example, may also be implanted, whereupon insulin is fed or supplied into the blood circulatory system until the glucose level has declined or fallen back below the adjusted normal value. The comparator will thereupon no longer produce an output signal, and the valve disposed between the blood circulatory system and the insulin receptacle is closed.

Finally, it has been proposed to provide for a fixed prior programming of the entire daily administration of a medication (more particularly, insulin), comprising moving the piston of a medication injector by means of a motor drive in accordance with said program in such a way that the desired daily dose is achieved while taking into account all fluctuations.

The apparatus according to U.S. Pat. No. 3 894 538 does have the advantage of achieving a continuous dosing up to the smallest values; however, the continuous feeding or ejection of medication also requires a continuous generation of pressure, and consequently, a constantly high requirement of input energy for the controlling electrodes, which requirement increases substantially when the rate of medication infeed increases. The apparatus according to U.S. Pat. No. 3 837 339 has an energy requirement which is relatively high, and furthermore does not permit fine dosing of the medication. The output of medication takes place rather at a constantly high rate, namely in each case for the duration of a comparator signal. Since the duration of medication infeed may be long owing to the inertia of the blood circulation and the electrical control system, there is the risk of continuous overdosing, whereby the supply of medication is rapidly exhausted, and more particularly, injury to the patient cannot be excluded, (an excess of insulin may result, for example, in life-endangering hypoglycemic shock). An apparatus comprising a piston injector has relatively high inertia on account of its design and mode of operation, and accordingly it does not permit sufficiently small dosings and requiries an excessively high expenditure of energy.

SUMMARY OF THE INVENTION

It is an object of the present invention to provide apparatus of the type described above which permits an optimally small dosing of the medication to be administered while requiring a minimum expenditure of energy.

According to the present invention, the above object is satisfied by a construction in which the pressure generator is a generator of overpressure which maintains the liquid present in the supply reservoir constantly at a pressure in excess of the pressure at the point at which the liquid is discharged, the dosing device comprising a controllable pilot valve for periodically releasing liquid from the supply reservoir to the body, said pilot valve being switchable to release position for dispensation of preselectable constant liquid volumes at periodic intervals that may be predetermined in accordance with an established treatment program specifically for the purpose of achieving fine dosage of the medication.

The generator for producing overpressure self-generates the energy for dispensing the liquid without requiring any supply of external energy. External energy must be provided solely for switching the pilot valve; however, this latter energy expenditure is low because the switching frequencies, or switching times of the desired fine dosing may be kept short. The use of the combination comprising an overpressure-generating device and a pilot valve according to the present invention therefore permits an application of desired fine dosing with the lowest possible expenditure of energy.

Further advantageous refinements or modifications of the present invention will hereafter become apparent to those skilled in the art.

Various embodiments of the present invention are disclosed in greater detail with reference to the attached drawings.

BRIEF DESCRIPTION OF THE DRAWING

FIG. 1 shows a basic circuit diagram of an embodiment in which the volume of the liquid to be dispensed or discharged is determined by controlling the flow of the liquid.

FIGS. 2 and 3 show pulse diagrams for possible flow control arrangements.

DETAILED DESCRIPTION

Figure 4:
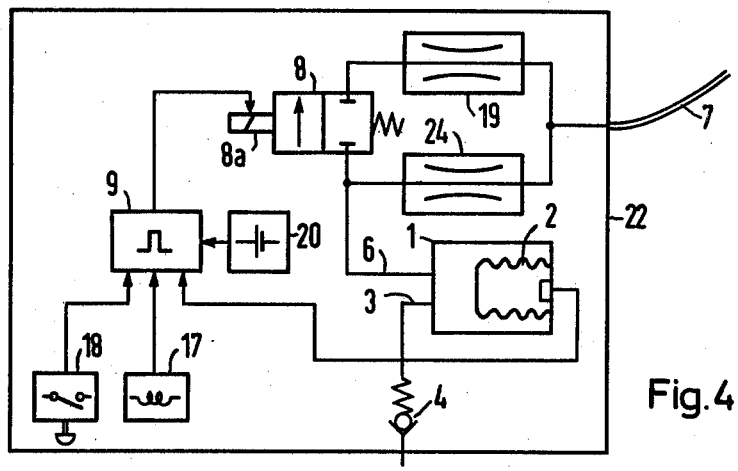
FIG. 4 shows a first modification of the embodiment according to FIG. 1.

In FIG. 1, reference numeral 1 designates a supply reservoir for a liquid medication, e.g. insulin. This supply reservoir, suitable, in practice has a volume for example of 10 cm$^3$. The liquid medication is present in such a concentration that the supply will be selectively sufficient for a period of time from 100 days up to 1 year.

Disposed within supply reservoir 1, there is provided an elastic receptacle 2 which in the present embodiment is in the form of a diaphragm bellows. Receptacle 2 is filled with a substance which is liquid at room temperature, and which has a vapor pressure of up to about 3 bars within the range of body temperature, the pressure is independent of the volume of receptacle 2. Chloroethane, for example, is a substane which satisfies these conditions.

The supply reservoir 1 is connected to a refill conduit 3 associated with a check valve 4. Through conduit 3 with check valve 4, it is possible, for example, to refill or replenish supply reservoir 1 with liquid medication, for example by using an injection syringe 5. Instead of using check valve 4, it is possible also to employ a self-closing or self-sealing plastic material or the like. Supply reservoir 1 is connected to a discharge conduit 6 for discharging or dispensing the medication via a thin feeding catheter 7 into the blood stream of the patient (not shown). Said catheter consists of a material which is compatible with the blood, for example polyurethane, and, if required, may also be heparinized, and it may also comprise, if need be, a safety relief or return valve disposed at its discharge point.

For controlling the discharge of the medication, there is provided in the present case a conventional-/electro-mechanical two-way valve 8 with locking zero-position, and an electomagnetic actuating device 8a. The switching of valve 8 to its open position takes place in response to switching pulses supplied by a switch pulse emitter or sender 9. The sequence frequency of the switching pulses, or their duration is selectively adjustable according to a predeterminable program.

A program-setting device 10 serves in the present case for presetting and controlling the course of the program. The program-setting device comprises in the present embodiment a control signal transmitter 11 (HF-modulated); program storage means 12 with time-signal transmitter (digital clock); a program input device 13 for feeding in the time and also the switch frequency program; an information or data transmitter 14 for indicating, for example, the state of the program and the time, and optionally including an acoustic or optical signal transmitter, for example, for signalling the consumption or intake of meals, or for indicating other stored information, for example, the number of caloric units to be consumed, medication and the like. A battery 15 serves for supplying the program-setting transmitter 10 with energy. An inductive coupling comprising coils 16 and 17 serves for transmitting the control signals of control signal transmitter 11 to switch pulse transmitter 9.

In addition to the program control arrangement, the switch pulse transmitter 9 further comprises a switching device 18 which is operated manually, consisting, for example, of a push-button or magnetic switch. Said manual switch serves, for example, for effecting individual corrections of the program as they may be required, for example, if there occurs a temporary or permanent failure of control signals of control signal transmitter 11 in program-setting device 10. Since the embodiment according to FIG. 1 is designated specifically for controlling the flow, the feeding conduit comprises a flow-limiting device or throttle 19 disposed in said feeding conduit between valve 8 and catheter 7. Said flow-limiting device consists, in the present case, of a capillary tube composed of glass or plastic material and having a length of approximately 10 mm, and an inner diameter of about from 5 to 50 $\mu$m. The inside diameter, and thus the flow can be adjusted individually by twisting said tube around its longitudinal axis. The arrangement furthermore comprises an energy supply source 20 for switch pulse transmitter 9 (which, source 20, for example, may be a battery, rechargeable accumulator, a PU capsule, or a bio-fuel cell). Finally, reference number 21 designates a temperature or pressure sensor which senses a change in temperature, for example, caused by fever, or any change of the effective pressure in over-pressure generator 2 caused by a temperature change, and by feeding a signal to pulse transmitter 9 counteracts any change of the flow of medication by adjusting the switching period of the valve inversely proportional to the change in pressure.

The disclosed embodiment provides for the medication-dispensing arrangement to be in the form of an implantable device, for which purpose all components of the medication-dispensing arrangement are accommodated within a housing 22 composed of tissue-compatible material, for example epoxy resin. If necessary, said housing may be provided with an additional metallic protection for eliminating interfering pulses (with the exception of the control signals of control signal transmitter 11). The program-setting device 10 can be carried extracorporally on the skin 23, for example, in the vest pocket or attached to a belt. However, it is, of course, understood that the program-setting device 10 may also be provided in the form of an implantable device, in which case its dimensions must be accordingly smaller.

FIGS. 2 and 3 show pulse diagrams of possible flow patterns of the medication as a function of time $t$. The pulses shown in the figures are the result of the switching frequency and the duration of the switching pulses of switch pulse transmitter 9 according to FIG. 1. The constant flow amplitudes are the result of the limiting of the flow by flow limiting device 19. The duration T of a switch (flow) pulse as well as the flow amplitude determine, in each case, the value of the volume of the medication in supply reservoir 1 which is to be discharge, or dispensed. In the embodiments according to FIGS. 1 to 3, the driving force for expelling or discharging the volumes of medication is exclusively generated by the pressure within overpressure receptacle 2.

The diagrams indicate that the dosing may be selectively determined by programmatically setting the switching frequency of the switching pulses of switch pulse transmitter 9 for valve 8, or their duration. In FIG. 2, for example, a more or less low daily basic rate B of medication discharge is obtained by adjusting the sequence frequency of the switching pulses for valve 8 to a low value (pulse spacing τ). Temporary peak values Sp of the dosing are specifically obtained by accordingly increasing the switching frequency. In the diagram according to FIG. 3, the basic rate is again obtained by selecting a low value for the switching frequency. However, as distinct from FIG. 2, the programmatic control of the peak values is achieved by changing pulse width T. For both the switching frequencies and pulse durations, values are recommended within an order of magnitude of from ⅓ to 3 per minute for the frequency, and of from 5 to 100 msec for the duration.

The basic rate of the dosing may also be adjusted in a modified manner by an additional flow limiting device having a predetermineable flow cross section, which device having a predetermineable flow cross section, which device may be provided in the form as shown in FIG. 1. Such a modification is shown by way of example in FIGS. 4 and 5.

In FIG. 4, an additional flow limiting device 24 for adjusting the basic rate is connected at its input side to discharge conduit 6 of supply reservoir 1 upstream of pilot valve 8. However, the output or outlet of said flow limiter is disposed parallel to flow limiter 19. Therefore, while a permanent basic flow of medication is administered to the patient by way of limiter 24 and catheter 7, valve 8 and limiter 19 serve for the respective adjustment and delivery of peak values.

Figure 5:
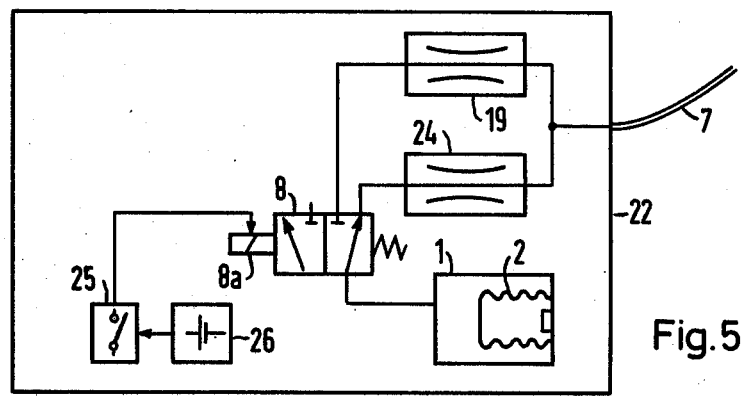
FIG. 5 illustrates a further or second modification of the embodiment according to FIG. 1.

FIG. 5 shows another modification using a conventional three-way valve 8, the limiting device 24 for the base rate and limiter 19 for the peak values being connected to the outlets of valve 8 in such a manner that a permanent flow is obtained when said valve is switched a first flow position, and the short-time peak value when said said valve is switched to the second flow position. The control may be effected in accordance with the embodiments according to FIGS. 1 to 4. However, an additional advantageous modification provides also for a control of valve 8 as a function of position switches or the like, which position switches are arranged on the patient, and signal certain conditions of the patient. For example, the switch member 25 in FIG. 5 may be a mercury switch operated by battery (for example of the type according to German published application 2 106 275) which, for example, senses conditions "patient rests" and "patient standing up, or sitting", and in accordance with such information, switches valve 8 to the delivery of a basic rate of medication flow via limiting device 24, or to an increased rate (peak rate) via limiting device 19.

Figure 6:
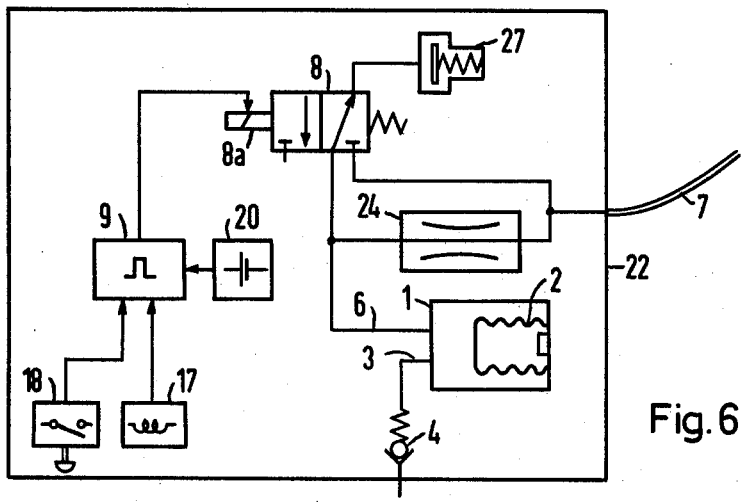
FIG. 6 shows a basic circuit diagram of an embodiment in which the volume to be discharged or dispensed is predetermined by an auxiliary supply reservoir.
Figure 7:
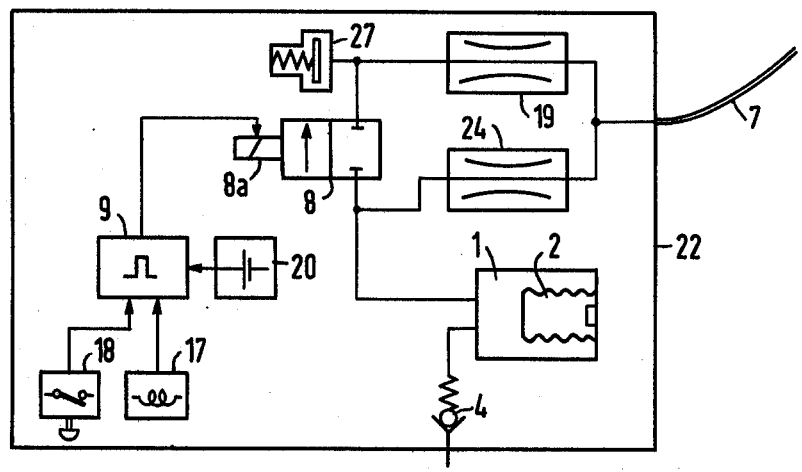
FIG. 7 illustrates a modification of the embodiment according to FIG. 6.

FIGS. 6 and 7 show embodiments of the present invention in which the value of the volume of medication to be dispensed is predeterminable not by means of flow control, but rather by means of an auxiliary reservoir 27 for the medication. For the purpose of storing a defined volume of medication, said auxiliary reservoir 27 is first connectable in each case to supply reservoir 1 by means of switch valve 8, and subsequently connectable to liquid feeding conduit 7 extending to the body of the patient in order to dispense said stored defined volume to the patient. Said auxiliary reservoir 27 may be provided in the form of a receptacle having a variable volume. When liquid medication is fed or stored in said reservoir against the pressure or a pressure-exerting means, for example, and elastic reservoir wall, or a piston disposed within reservoir 27 in accordance with the embodiment, the volume of auxiliary reservoir 27 will increase only by a predetermined value, and return to its original value after the stored liquid medication has been discharged. However, auxiliary reservoir 27 may be in the form of a receptacle having a constant volume, in which the liquid medication to be stored is compressed to a defined overpressure value, and the discharge of a defined volume is subsequently effected as a result of decompression. In the embodiment according to FIG. 6, the flow limiting device 24 again serves for adjusting the basic daily rate of dispensation, whereas the auxiliary reservoir 27 in combination with valve 8 determines periodic peak values. In the embodiment according to FIG. 7, a flow limiting device 19 is also connected downstream of auxiliary reservoir 27, which limiter 19 smoothens the peak value discharge from auxiliary reservoir 27.

The present invention is not intended to be limited to the embodiments described in the foregoing, but also contemplates other modifications which are within the scope and spirit of the invention as defined in the attached claim.

What is claimed is:

1. An apparatus for infusing of liquid into a human or animal body comprising a catheter for extending into a blood stream of the body, a supply reservoir for the liquid having a discharge conduit, pressure generator means for applying a pressure on the liquid in the supply reservoir to cause discharge through the discharge conduit, and an adjustable dosing means attached between the catheter and the discharge conduit for producing a desired infusion rate in the catheter, said pressure generator means being an over-pressure generator operating without an external energy source and constantly maintaining the liquid in the supply reservoir at an excess pressure as compared with the pressure prevailing at the point of the liquid discharge from the catheter, said adjustable dosing means including means for providing an infusion flow at a base rate and means including a controllable switching valve means for periodically producing an infusion flow at a peak value, said switching valve means being operable by a switching pulse, a switch pulse transmitter means for producing the switching pulse with one of the repetition rates and duration of the switching pulses being programmatically predetermined for the purpose of producing a periodic release of the liquids from the supply reservoir through the catheter to the body at pre-programmed time intervals, and a position switch means arranged on the patient for providing signals depending on certain positions assumed by the patient, said position switch means being coupled to said valve means for regulating said valve means in dependence of said position switch means.

2. An apparatus according to claim 1 wherein said position switch means is adapted to pick up conditions of "patient resting" and "patient standing or sitting" for switching the valve means for selective discharge of a basic rate and an increased rate, a first limiting means coupled to said valve means and in one position of said position switch means effecting discharge at the basic rate, and a second limiting means coupled to said valve means and in a second position of said position switch means effecting discharge at an increased peak rate.

3. An apparatus for infusing of a liquid into a human or animal body comprising a catheter for extending into a blood stream of the body, a supply reservoir for the liquid having a discharge conduit, pressure generator means for applying a pressure on the liquid in the supply reservoir to cause discharge through the discharge conduit, and an adjustable dosing means attached between the catheter and the discharge conduit for producing a desired infusion rate in the catheter, said pressure generator means being an over-pressure generator operating without an external energy source and constantly maintaining the liquid in the supply reservoir at an excess pressure as compared with the pressure prevailing at the point of the liquid discharge from the catheter, said adjustable dosing means including means for providing an infusion flow at a base rate and means including a controllable switching valve means for periodically producing an infusion flow at a peak value, said switching valve being operable by a switching pulse, a switch pulse transmitter means for producing the switching pulse with one of the repetition rates and duration of the switching pulses being programmatically predetermined for the purpose of producing a periodic release of the liquid at a peak rate from the supply reservoir through the catheter to the body at pre-programmed time intervals, said means for providing a flow rate at a base rate comprising a flow limiting device having a preselected flow cross section, said flow limiting device being connected between the discharge conduit and the catheter and parallel with the switching valve means so that the base rate is discharged regardless of actuation of the switching valve means.

4. Apparatus according to claim 3 comprising an auxiliary supply reservoir means determining the value of the liquid volume to be discharged, said valve means being coupled to said auxiliary reservoir means to connect the same first to the supply reservoir for the purpose of storing a defined volume of liquid to said auxiliary reservoir means and subsequently for discharge of the stored defined volume to the body.

5. Apparatus according to claim 4 wherein said auxiliary supply reservoir means is a receptacle having a variable volume with a displaceable pressurized wall, said volume increasing by only a fixed value upon storing of liquid in said receptacle against the pressure of said wall and returning to its original volume upon discharge of the stored volume of liquid.

6. Apparatus according to claim 4 wherein said auxiliary supply reservoir means is a receptacle having a constant volume, the liquid to be stored being compressed in said receptacle to a defined overpressure value, and the discharge of a defined volume being effected by decompression of said receptacle.

7. An apparatus for infusing of liquid into a human or animal body comprising a catheter for extending into a blood stream of a body, a supply reservoir for the liquid having a discharge conduit, pressure generator means for applying a pressure on the liquid in the supply reservoir to cause discharge through the discharge conduit, and an adjustable dosing means attached between the catheter and the discharge conduit for producing a desired infusion rate in the catheter, said pressure generator means being an over-pressure generator operating without an external energy source and constantly maintaining the liquid in the supply reservoir at an excess pressure as compared with the pressure prevailing at the point of the liquid discharge from the catheter, said adjustable dosing means including means for providing an infusion flow at a base rate and means including a controllable switching valve means for periodically producing an infusion flow at a peak value, said switching valve means being operable by a switching pulse, a switch pulse transmitter means for producing the switching pulse with one of the repetition rates and duration of the switching pulses being programmatically predetermined for the purpose of producing a periodic release of the liquids from the supply reservoir through the catheter to the body at pre-programmed time intervals, said over-pressure generator including a sensor means for sensing a change in one of the temperature and pressure of the over-pressure generator, said sensor means being coupled to the switch pulse transmitter means to effect a change of liquid flow by adjusting the switch pulse duration in inverse proportion to the adjusting the switch pulse duration in inverse proportion to the change in pressure in the over-pressure generator.

8. Apparatus according to claim 7 comprising a manual switch for manually transmitting a program to the switch pulse transmitter means.

9. Apparatus according to claim 7 comprising a program transmitter means coupled to said switch pulse transmitter means for controlling the switching frequency and duration of the switching pulses of said switch pulse transmitter means for said valve means.

10. Apparatus according to claim 9 wherein said program transmitter means comprises a program storage means with time transmitter, a program input device coupled to the storage means for feeding a time and switch frequency program thereto, a data transmitter means coupled to the storage means for indicating the state of the program and the time.

* * * * *